United States Patent [19]

Amstutz et al.

[11] Patent Number: 4,715,860
[45] Date of Patent: Dec. 29, 1987

[54] POROUS ACETABULAR HIP RESURFACING

[75] Inventors: Harlan C. Amstutz, Pacific Palisades; J. Michael Kabo, Los Angeles, both of Calif.

[73] Assignee: The Regents of the University of California, Berkeley, Calif.

[21] Appl. No.: 768,871

[22] Filed: Aug. 23, 1985

[51] Int. Cl.⁴ .............................................. A61F 2/34
[52] U.S. Cl. ...................................................... 623/22
[58] Field of Search ...................... 623/16, 17, 18, 19, 623/20, 21, 22, 23

[56] References Cited

U.S. PATENT DOCUMENTS

| 3,605,123 | 9/1971 | Hahn | 623/16 |
| 3,840,904 | 10/1974 | Tronzo | 623/22 |
| 3,982,281 | 9/1976 | Giliberty | 623/23 |
| 4,123,806 | 11/1978 | Amstutz | 623/22 |

FOREIGN PATENT DOCUMENTS

| 0159510 | 4/1984 | European Pat. Off. | 623/22 |
| 0137664 | 4/1985 | European Pat. Off. | 623/22 |
| 3228113 | 2/1984 | Fed. Rep. of Germany | 623/22 |
| 2548012 | 1/1985 | France | 623/22 |
| 1527498 | 10/1978 | United Kingdom | 623/22 |

Primary Examiner—Richard J. Apley
Assistant Examiner—David J. Isabella
Attorney, Agent, or Firm—Poms, Smith, Lande & Rose

[57] ABSTRACT

An artificial hip joint includes a socket or acetabular portion and a femoral portion secured to the upper leg bone or femur. A continuous metal acetabular cup for an artificial hip joint is provided with a right cylindrical portion and chamfered dome which is of porous titanium or other suitable material, including a coating of either sintered fibers or sintered small particles such as spheres, to encourage early bone ingrowth, following force fit insertion of the cup into the acetabulum. A plastic insert having a central recess for receiving the femoral ball, is inserted into the cup and includes interlocking elements for holding the plastic insert firmly into the metal cup and against rotation, and a flange extending over the lip of the metal cup to preclude metal to metal contact.

17 Claims, 8 Drawing Figures

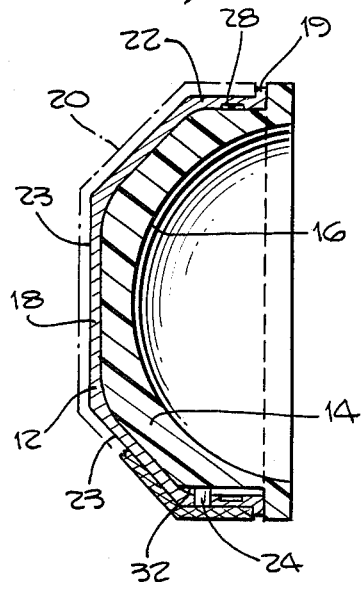
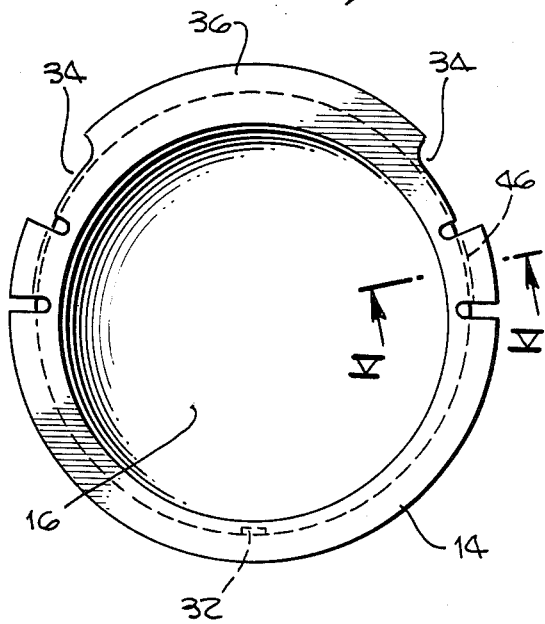
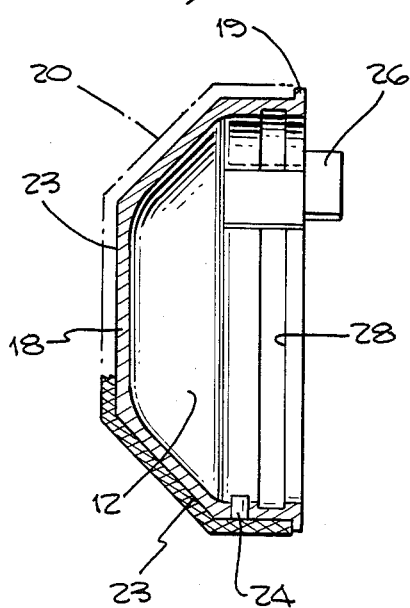
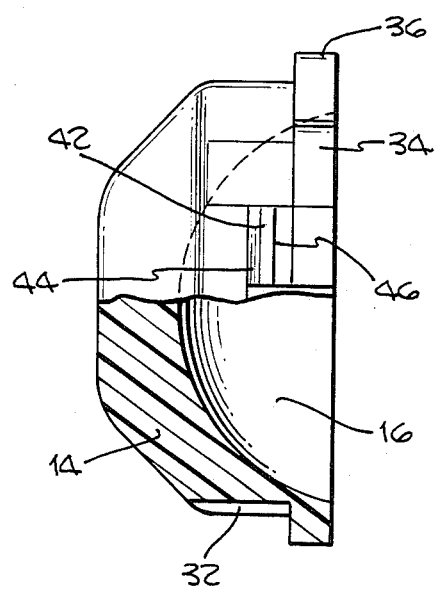

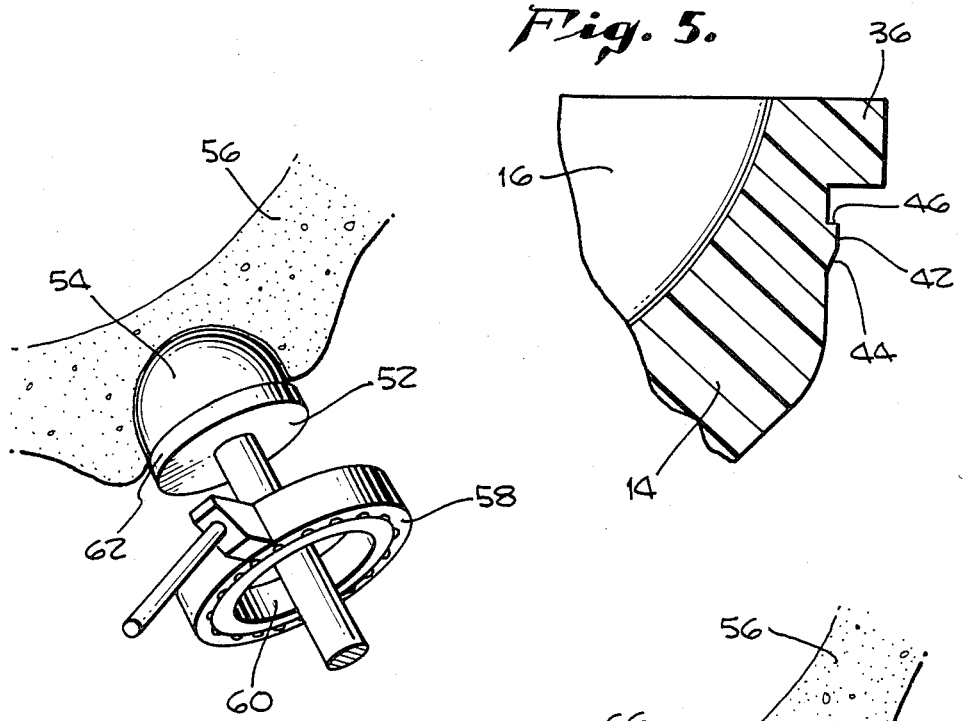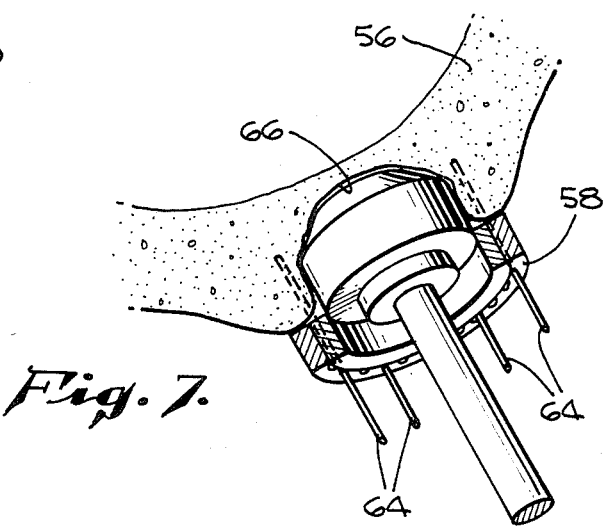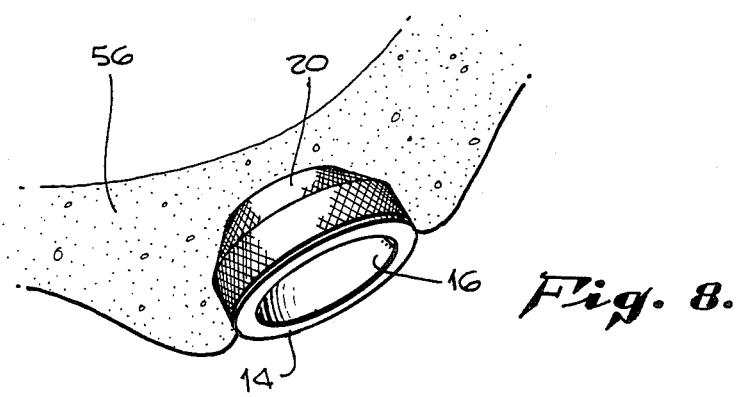

POROUS ACETABULAR HIP RESURFACING

GOVERNMENT RIGHT

This invention was made with Government support under Grant No. AM 20333 awarded by the Department of Health and Human Services. The Government has certain rights in this invention.

FIELD OF THE INVENTION

This invention relates to artificial hip joints.

BACKGROUND OF THE INVENTION

Problems with diseased and arthritic hip joints have been with the human race for many years. Since early in the present century, various proposals and operative techniques have been proposed for partial or complete replacement of the hip joint. One prior arrangement which has met with considerable success is disclosed in U.S. Pat. No. 4,123,806, granted Nov. 7, 1978, to Dr. Harlan C. Amstutz, et al., with Dr. Amstutz being one of the co-inventors in the present case. Other prior proposals are shown in U.S. Pat. Nos. 4,173,797, granted Nov. 13, 1979; 3,894,297, granted July 15, 1975; 4,164,794, granted Aug. 21, 1979; and British Patent No. 2,117,646, published Oct. 19, 1983.

With regard to the hip socket, or acetabular components, some problem has been encountered, particularly with more active patients, in the loosening of the component. More particularly with the frequent stressing of the hip joint as a person walks, if the joint is not fairly rigid and securely fastened into the hip joint, the resultant micromovements will become cumulative, and the loosening of the hip joint prosthesis will result. Another problem has been the limited amount of bone which may be available near the hip socket. Thus, with some proposed prosthesis, such as that shown in U.S. Pat. No. 3,894,297, the prosthesis is so large, that there may be insufficient surrounding bone structure, in some cases to properly retain and support the fixture. In other cases, there have been materials failures, and the cements which have been used in some cases have failed, in the case of some active patients. In addition, the problem of accurately fitting the prosthesis securely and tightly in place is a serious problem, particularly under the conditions encountered during the course of a major operation.

Accordingly, a principal object of the present invention is to provide an acetabular artificial hip joint component which uses minimum space and which will be firmly and permanently secured in position through biological ingrowth.

SUMMARY OF THE INVENTION

In accordance with the present invention, an artificial hip joint includes a socket or acetabular portion including an outer metal shell or cup having a peripheral right cylindrical area and chamfered dome coated with porous metal, such as titanium, and an inner plastic cup formed of high density plastic such as polyethylene or the like.

In the course of the method in accordance with the present invention, a reamer guide is initially carefully located over the hip joint socket, and then a cylindrical-chamfer reamer is employed in the defective hip joint, to provide a right cylindrical and chamfered surfaces. This cylindrical opening is made preferably slightly less in diameter than the right cylindrical diameter of the metal cup to be used, as mentioned above. Then the porous metal surfaced cup is force fitted into the reamed hip joint opening, to thus provide secure seating, and one in which rapid ingrowth of bone into the porous titanium is facilitated.

In accordance with a collateral feature of the invention, the plastic insert is provided with a recess along one of its outer surfaces to interfit with a matching pin which is located on the side of the metal cup, thus assuring radial orientation of the plastic cup. In addition, the metal cup is provided with a peripheral recess just inside its open lip, into which at least a pair of locking protrusions from the plastic insert are received. The metal cup may also have two slightly protruding metal parts along its outer lip. The plastic insert is provided with a peripheral flange which overlies the outer lip of the metal cup; but this outer flange is cut away in two areas to receive the metal protrusions, thus assisting in the orientation and preventing movement or other rotation of the plastic insert. The metal protrusions preferably do not extend beyond the flange on the plastic insert.

Other objects, features and advantages of the invention will become apparent from a consideration of the following detailed description and from the accompanying drawings.

BRIEF DESCRIPTION OF THE DRAWINGS

FIG. 1 is a cross-sectional view of the acetabular component of an artificial joint, illustrating the principles of the present invention;

FIG. 2 is a cross-sectional view of the cup-shaped outer metallic shell, with its right cylindrical peripheral surface;

FIG. 3 is a partial cross-sectional view of the plastic insert employed with the metal cup of FIG. 2;

FIG. 4 is a front view of the plastic insert taken from the open side thereof;

FIG. 5 is an enlarged cross section taken along lines V—V of FIG. 4;

FIG. 6 is a view showing the first step in locating the acetabular reamer guide;

FIG. 7 shows a reamer forming a portion of the recess for the acetabular component of FIG. 1; and FIG. 8 shows the artificial hip joint acetabular component inserted in place.

DETAILED DESCRIPTION

Referring more particularly to the drawings, FIG. 1 shows the acetabular component, including the outer metal cup 12, and the plastic insert 14. The inner surface 16 of the plastic insert 14 is spherical in its configuration, and it is designed to mate with the femoral component which is often a round metal ball. The spherical surface to mate with large diameter femoral balls provides 160 degrees of coverage for all sizes to insure consistent anthropometric features for a wide range of patient sizes. The metal cup 12 is preferably formed of an inner continuous metal cup 18 of titanium alloy or other suitable material, and an outer layer 20 of porous titanium fibers or spheres. The titanium metal cup, which is solid, may be about 1½ millimeters thick, and the layer of porous titanium wires or spheres is also about 1½ millimeters thick. The wires are preferably about 1-10th of a millimeter in diameter and are usually approximately ¾" to 2" in length. They are pressed into place and sintered, so that the average pore size or space is about 200 microns to 500 microns, and preferably approximately 350 microns or about 0.35 millimeters. A similar pore size of approximately 350 microns is preferred when spheres or other small particles are employed instead of the wires. With the total thickness of the layer being about 1½ millimeters, with the wires being in the order of 100 microns in diameter, and the pore size being approximately 350 microns, there is a complex passageway of spaces in behind the outer sintered wires. This is most advantageous for interlocking bone ingrowth and for permanently securing the acetabular component to the hip.

It is further noted that the sidewall 22 is of right cylindrical configuration, and extends for at least one-half of a centimeter. As will be discussed in greater detail below, it is intended that the cup 12 be force fitted into the acetabular hip joint cavity with accurate tolerances, so that the surrounding bone will be in intimate contact with the porous outer surface 20 of the component so that rapid bone ingrowth is encouraged and will commence substantially immediately. It is further noted that the remainder of the configuration consists of a chamfered portion ending in a flat apex 23. This is to conserve space and maintain close apposition to the bone.

A thin metal ring 19 overlaps the exposed porous material at the mouth of the shell but does not cover the full extent. This is to prevent dislodgement of the porous material from the metal shell as the unit is press fit into place.

In this regard, several factors must be present in order to obtain rapid ingrowth. Specifically, the metal acetabular cup must (1) have the proper porous outer surface, (2) the outer porous surface of the cup must be maintained in an intimate fixed position with respect to the mating surface of the bone, despite the repeated stressing and application of forces to the cup during normal walking or other movement of the patient. When a fully hemispherical metal cup is used, it is not practical to consistently get a precise fit between the bone socket and the outer surface of the cup, as slight errors in the depth and diameter of reaming will preclude the necessary precision fit. Additionally, hemispherical designs require pins, screws or other forms of adjuvant fixation to achieve initial stability and maintain metal to bone contact. Similarly, the cup may not be slotted or unduly flexible so that the outer surfaces of the cup will have micromovements as the joint is stressed. If these micromovements between the outer surface of the metal shell and the mating bone surfaces occur, bone ingrowth cannot get started, and is immediately inhibited. These problems are avoided using a solid, nonslotted metal shell, having a substantial right cylindrical portion adjacent the outer lip thereof, making a slight interference fit with the reamed socket in the hip bone.

With regard to other features of the construction, it is desired that the inner plastic component 16 be secured against rotation, and against removal from the metal cup, once it is inserted into it. With reference to FIG. 2 of the drawings, rotation of the inner plastic cup is prevented by the use of the pin 24 as well as the two protruding metal tabs 26. The metal cup 12 is also provided with a peripheral recess 28 into which interlocking members from the plastic cup fit and engage.

The inner plastic cup 14 per se is shown in FIGS. 3, 4 and 5. The cross-sectional view of FIG. 5 is taken along lines V—V of FIG. 4. FIG. 3 is a partial cross-sectional view, while FIG. 4 is a view from the open side of the plastic cup or insert 14 having spherical recess 16. Shown in dashed lines in FIG. 4 and as a slot in FIG. 3, is the recess 32 into which the pin 24 extends. Also shown in FIG. 4 are the two recesses 34 in the outwardly extending flange 36 of the plastic insert 16. These recesses 34 receive the outwardly extending tabs 26 from the cup 12, as shown in FIG. 2. The flange 34 normally extends over the entire outer lip of the metal cup 12, and avoids the possibility of metal-to-metal contact between the femoral component which normally has a protruding metal ball, and the titanium cup 12. Incidentally, the metal alignment tabs 26 are of slightly less elevation or extent than the thickness of the flange 36, so that the outer tips of the tabs 26 do not protrude beyond the outer surface of the flange 36.

Attention is now directed to FIG. 5 of the drawings and to the location at lines V—V in FIG. 4, where the section of FIG. 5 is taken. Now, with reference to FIG. 5, the locking tab or element 42 has a tapered surface 44 to facilitate press fitting the element 16 into the metal cup 12. In addition, once it has been pressed into place, the surface 46 engages the recess 28 in the metal cup 12 and holds the plastic insert in place.

Consideration will now be given to the procedure of inserting the acetabular component, in connection with FIGS. 6, 7 and 8 of the drawings. Incidentally, a number of medical steps involved in the operation procedure are set forth in the prior U.S. Pat. No. 4,123,806, cited hereinabove.

Now, with reference to FIG. 6 of the drawings, an acetabular reamer guide locating member 52 is initially inserted into the hip joint socket 54 in the acetabulum or hip bone 56. In FIG. 6 the reamer guide 58 with plastic insert is shown in the process of being advanced over the reamer guide locating member 52. From the position shown in FIG. 6 the reamer guide 58 is advanced until it engages the acetabulum, with the central opening 60 of the reamer guide 58 in engagement with the outer cylindrical surface 62 of the reamer guide locating member 52, and thus being precisely centered on the hip socket. As indicated in FIG. 7, three threaded pins with locking nuts indicated at reference numeral 64 are employed to hold the reamer guide 58 in place. A single reaming step is then conducted, serving to ream the acetabular bone 66 of the hip joint socket to the proper right cylindrical and chamfered configuration for receiving the titanium cup 12. The depth of reaming is determined by the height of the reamer and more precisely by an additional frosted translucent template which is of the same profile as the reamed bone surface with a height equal to that of the component to be used. When reaming has been successully completed, this template indicates contact with the freshly prepared bone surfaces an is totally resident in the acetabular cavity. In each case, the reamer guide 58 accurately controls the positioning of the reamer with respect to the hip joint socket.

FIG. 8 shows the metal cup 12 having been inserted into the reamed hip joint socket. The relative diameters of the reamed opening and the peripheral right cylindrical sidewalls of the titanium cup 12, are such that a force fit of the insert 12 into the hip joint socket is required. This interference is preferably 0.75 mm to 1.0 mm diametral difference. This force fit of the porous outer surface of the cylindrical cup 12 firmly secures the component in place, and encourages early bone ingrowth into the porous outer surface of the component, as mentioned above.

Incidentally, the insertion of the plastic insert is normally deferred until this point in time in the operation. The reason for this delay is the possible alternative femoral component artificial joint units which may be employed. These femoral components may differ in the size of the metal ball which will mate with the acetabular component; accordingly, alternative spherical recess diameters, as shown at 16 in FIG. 1 may be employed, with lesser diameters than that shown, being used for certain types of femoral components.

Incidentally, concerning additional dimensions and configuration of the acetabular component, it may be noted that the inner surface of the metal cup 12 may be rounded or of identical geometry to the outer metal surfaces. In any case the internal geometry of the metal shell 12 should match the outer profile of the plastic liner 14 to insure sufficient support of the plastic during weight bearing by the patient. Incidentally, the plastic insert may be formed of high density polyethylene. With regard to the dimensions of the acetabular component, it is made in a number of sizes, to accommodate patients of different ages and physical configuration. At present it is made in five different sizes, with the outer diameter of the metal cup ranging from 46 mm minimum to 51 mm maximum and the total depth of the metal cup ranging from 20 mm minimum to 27.5 mm maximum. The spherical surface 16 of the plastic component 14 should maintain the same arc of coverage on the femoral ball irrespective of size. This will insure consistent joint stability and range of motion for all sizes. Additionally, the spherical surface 17 is less than a full hemisphere to increase the range of motion possible. In addition, as noted above, the thickness of the solid titanium shell is about 1.5 mm and the thickness of the sintered wire mesh layer is approximately 1.5 mm. It is also noted that the important right cylindrical portion of the metal cup ranges in extent from a minimum of 8.65 mm to a maximum of 11.75 mm. Accordingly, in all embodiments there is a substantial right cylindrical area, more than one-half of a centimeter, and extending entirely around the cup, which will make a force fit with the reamed socket, to promote rapid bone ingrowth and permanent fixation.

In conclusion, it is to be understood that the foregoing description and the associated drawings, merely relate to one illustrative preferred embodiment of the invention. Other alternative arrangements may be employed without departing from the spirit and scope of the present invention. Thus, by way of example and not of limitation, the titanium mesh or porous surface which may be employed, or other suitable materials, may be formed of fine wire or spheres which have been sintered together, or other arrangements with a comparable pore size and the capability and affinity for bone ingrowth locking. In addition, a larger number of locking tabs and/or different mechanically interlocking arrangements for precluding rotation of the plastic insert relative to the metal cup, or its easy separation therefrom could be used. Accordingly, the present invention is not limited to the device as described in detail hereinabove and as shown in the drawings.

What is claimed is:

1. An acetabular component for an artificial hip joint comprising:
   a continuous metal cup having a rim, said cup having a diameter of between about four and seven centimeters, said cup having an outer coating of a porous metallic material having an affinity for bone ingrowth, the outer periphery of said cup extending from the rim thereof having a aright cylindrical configuration extending from the rim thereof having a right cylindrical configuration extending for at least one-half centimeter away from the rim thereof;
   a hollow plastic insert including means for firmly securing said insert into said metal cup after said cup is in place in the patient, said plastic insert having a central opening having a substantially spherical surface for receiving the ball of the femoral component of the artificial hip joint;
   said cylindrical surface of said cup extending for the greater portion of the periphery of said cup, said cylindrical surface extending for in the order of one-half or less of the total depth of said prostheses, and then being directed inwardly toward the bottom of said plastic insert and generally following the configuration of said spherical surface to minimize the necessary bone removal and to avoid penetration of the acetabulum; and
   said cup being free of outwardly directed elements which might otherwise interfere with full press-fit seating of said cup;
   whereby a force fit of the right cylindrical surface of the acetabular component encourages early bone growth into the porous outer coating thereof, and increased permanency of the artificial joint.

2. An acetabular component for an artificial hip joint as defined in claim 1 wherein said metal cup and said porous outer surfaces are made of titanium, a titanium alloy, or other medically inert materials.

3. An acetabular component for an artificial hip joint as defined in claim 1 wherein said porous outer coating has a pore size of between about 200 and about 500 microns.

4. An acetabular component for an artificial hip joint as defined in claim 1 wherein said plastic insert is formed of high density polyethylene.

5. An acetabular component for an artificial hip joint as defined in claim 1 wherein said plastic insert has a peripheral flange which overlies the outer rim of said metal cup.

6. An acetabular component for an artificial hip joint as defined in claim 5 wherein said metal cup includes two outwardly extending protrusions, and wherein the flange of said plastic insert is notched to receive these protrusions, to provide fixed relative angular positioning of said cup and said insert.

7. An acetabular component for an artificial hip joint as defined in claim 1 wherein the side walls of said metal cup are between two and four millimeters thick, with the outer porous metal layer being between one and two millimeters thick, and the solid continuous inner cup also being between one and two millimeters thick.

8. An acetabular component for an artificial hip joint as defined in claim 1 wherein said porous outer coating is formed of sintered titanium wires each having a thickness in the order of about one twentieth of a millimeter to about one-fifth of a millimeter.

9. A method of forming an artificial hip joint socket comprising the steps of:
   preparing a metal cup for an artificial hip joint acetabular component with the cup having an outer coating of a porous metallic material having a right cylindrical configuration extending around the greter portion of the periphery of said cup, for at least one-half centimeter from the rim thereof said cylindrical surface extending for in the order of one-half or less of the total depth of said prostheses, and then being directed inwardly toward the bottom of said plastic insert and generally following the configuration of said spherical surface to minimize the necessary bone removal and to avoid penetration of the acetabulum; said cup having a predetermined cylindrical diameter and said cup being free of outrwardly extending sharp projection or other elements which might otherwise interfere with fujll press-fit seating of said cup;

inserting a centering guide into the hip socket which is to receive the metal cup;

securely locating a reamer guide on the acetabular and centered on the hip socket using said centering guide for alignment;

reaming a cylindrical surface having a very slightly smaller diameter than said predetermined diameter in the hip socket concurrent with chamfer reaming, using said reamer guide for alignment; and securing said cup in place by forcefully inserting said cup into the reamed hip joint socket, with no sharp points extending into the adjacent bone;

whereby rapid bone ingrowth into the porous outer surface of said cup is promoted by the intimate engagement between said cup and the adjacent bone surface.

10. A method as defined in claim 9 comprising the additional step of securing a plastic insert into said metal cup, said plastic insert having a spherical recess for receiving the ball of an artificial femoral joint component.

11. A method as defined in claim 9 including the steps of successively reaming the cylindrical side walls of the hip joint, and reaming the bottom of the hip joint to conform in depth and configuration to said metal cup.

12. A method as defined in claim 10 including the step of locking said plastic insert into place in said metal cup against both axial and rotational movement.

13. An acetabular assembly for an artificial hip joint comprising:

a continuous titanium metal cup, said cup having a diameter of between about four and seven centimeters, said cup having an outer coating of a porous sintered titanium metallic material having an affinity for bone ingrowth, the outer periphery of said cup extending from the rim thereof having a right cylilndrical configuration extending for at least one-half centimeter away from the rim thereof;

said assembly being free of outwardly extending protrusions from said cup which might otherwise interfere with full press-fit seating;

a hollow plastic insert including means for firmly securing said insert into said metal cup after said cup is in place in the patient, said plastic insert having a central opening having a substantially spherical surface for receiving the ball of the femoral component of the artifical hip joint; and said cylindrical surface of said cup extending for the greater portion of the periphery of said cup, said cylindrical surface extending for in the order of one-half or less of the total depth of said prostheses, and then being directed inwardly toward the bottom of said plastic insert and generally followiwng the configuration of said spherical surface to minimize the necessary bone removal and to avoid penetration of the acetabulum;

whereby a force fit of the right cylindrical surface of the acetabular component encourages early bone growth into the porous outer coating thereof, and increased permanency of the artificial joint.

14. An acetabular assembly for an artificial hip joint as defined in claim 13 wherein said porous outer coating has a pore size of between about 200 and about 500 microns.

15. An acetabular assembly for an artificial hip joint as defined in claim 13 wherein said plastic insert is formed of high density polypropylene.

16. An acetabular assembly for an artificial hip joint as defined in claim 13 wherein said plastic insert has a peripheral flange which overlies the outer rim of said metal cup.

17. An acetabular assembly for an artificial hip joint as defined in claim 13 wherein the side walls of said metal cup are between two and four millimeters thick, with the outer porous metal layer being between one and two millimeters thick, and the solid continuous inner cup also being between one and two millimeters thick.

* * * * *